United States Patent
Sato

(10) Patent No.: US 8,111,878 B2
(45) Date of Patent: Feb. 7, 2012

(54) VEIN AUTHENTICATION DEVICE AND VEIN AUTHENTICATION METHOD

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 595 days.

(21) Appl. No.: 12/352,965

(22) Filed: Jan. 13, 2009

(65) Prior Publication Data

US 2009/0214083 A1 Aug. 27, 2009

(30) Foreign Application Priority Data

Jan. 16, 2008 (JP) ................ P2008-006944

(51) Int. Cl.
*G06K 9/00* (2006.01)
*H04N 5/222* (2006.01)

(52) U.S. Cl. ............. 382/115; 382/274; 348/370
(58) Field of Classification Search ........... 382/100, 382/103, 106, 107, 108, 115, 116, 124, 126, 382/128, 132, 162, 168, 173, 181, 190, 199, 382/219, 232, 254, 274, 276; 348/370; 235/462.06
See application file for complete search history.

(56) References Cited

U.S. PATENT DOCUMENTS

| | | | |
|---|---|---|---|
| 6,688,523 B1 * | 2/2004 | Koenck | 235/462.06 |
| 7,660,446 B2 * | 2/2010 | Abe | 382/124 |
| 7,903,847 B2 * | 3/2011 | Higuchi | 382/126 |
| 7,978,259 B2 * | 7/2011 | Matsuo et al. | 348/370 |
| 8,000,503 B2 * | 8/2011 | Kamata et al. | 382/115 |
| 2006/0023921 A1 * | 2/2006 | Saitoh et al. | 382/115 |
| 2010/0142770 A1 * | 6/2010 | Hayasaka et al. | 382/124 |

FOREIGN PATENT DOCUMENTS

JP 2006-288872 10/2006

* cited by examiner

*Primary Examiner* — Seyed Azarian
(74) *Attorney, Agent, or Firm* — Finnegan, Henderson, Farabow, Garrett & Dunner, L.L.P.

(57) ABSTRACT

A vein authentication device according to the present invention includes an imaging part for continuously imaging a portion of venation present inside a finger by near-infrared light scattered inside the finger by irradiating a finger surface with the near-infrared light while continuously imaging a portion of fingerprints present on the finger surface or inside the finger by reflected light reflected on the finger surface or inside the finger, a motion vector detection part for detecting a motion vector of the fingerprints, an image synthesis part for synthesizing images picking up a portion of the fingerprints to generate an image of the fingerprints and synthesizing images picking up a portion of the venation to generate an image of the venation, a vein pattern extraction part for extracting a vein pattern from the image of the venation, and an authentication part for performing authentication processing.

7 Claims, 8 Drawing Sheets

000# VEIN AUTHENTICATION DEVICE AND VEIN AUTHENTICATION METHOD

CROSS-REFERENCE TO RELATED APPLICATION

The present invention contains subject matter related to Japanese Patent Application JP 2008-006944 filed in the Japan Patent Office on Jan. 16, 2008, the entire contents of which being incorporated herein by reference.

BACKGROUND OF THE INVENTION

1. Field of the Invention

The present invention relates to a vein authentication device and a vein authentication method.

2. Description of the Related Art

Biometric identity verification is a very important technology to protect rights in a future network society. Particularly in business transactions on the Internet in which another person can pose as a person in question and steal money, content, and privileges over the network, biometric identity verification has gained attention as a technology to protect such fields that are difficult to resolve by encryption alone. However, it is difficult for fingerprints and irises to resolve an issue of forgery. In this respect, a personal authentication technology using a pattern of vein in an area that is difficult to image easily from outside is expected as a next-generation biometric identity verification due to high-level determination precision and difficulty of forgery and impersonation.

Such a biometric identity verification technology includes, for example, a fingerprint authentication technology and a vein authentication technology. The fingerprint authentication technology has issues of presence of about 4% of users who are disabled to register their fingerprints and resistance to attacks using residual fingerprints for posing, but has an advantage that sensors can be miniaturized because images can easily be synthesized even by a scan type system using line sensors or area sensors. On the other hand, the vein authentication technology expected as a next-generation authentication technology having less such issues uses larger sensors and thus, it is difficult to mount the technology in mobile devices. Particularly in an imaging system in which transmission images of vein are used, planar structuring of a device is difficult due to strict limitations on the position of a light source.

Thus, in order to realize miniaturization of a device using vein authentication technology, Japanese Patent Application Laid-Open No. 2006-288872 uses a method by which the scan speed of a finger is detected from a picked-up image to reconfigure a picked-up finger vein image using a graded index lens array.

SUMMARY OF THE INVENTION

Here, the lens array described in Japanese Patent Application Laid-Open No. 2006-288872 adopts a method by which a finger surface is taken by using a plurality of lens arrays having different focal lengths to generate a plurality of images of the same location on the finger surface taken with different focal lengths and an overall image is reconstructed by using only well-focused images from the plurality of obtained images and thus, there is an issue that a plurality of lens arrays to image the same location on the finger surface becomes necessary, increasing the size of the lens array. Further, when a lens array is used, there is an issue that costs necessary for manufacturing devices increase depending on the size of the lens array because an image sensor having the same size as a projected area of the lens array becomes necessary.

Thus, the present invention has been developed in view of the above issues and it is desirable to provide a new and improved vein authentication device promoting miniaturization of the device and capable of picking up a wide-ranging vein image and a vein authentication method.

According to an embodiment of the present invention, there is provided a vein authentication device including an imaging part for continuously imaging a portion of venation present inside a finger by near-infrared light scattered inside the finger by irradiating a finger surface with the near-infrared light while continuously imaging a portion of fingerprints present on the finger surface or inside the finger by reflected light reflected on the finger surface or inside the finger, a motion vector detection part for detecting a motion vector of the fingerprints based on a plurality of images picking up a portion of the fingerprints, an image synthesis part for synthesizing images picking up a portion of the fingerprints based on the motion vector of the fingerprints to generate an image of the fingerprints and synthesizing images picking up a portion of the venation based on the motion vector of the fingerprints to generate an image of the venation, a vein pattern extraction part for extracting a vein pattern from the image of the venation, and an authentication part for performing authentication processing based on the extracted vein pattern, wherein the imaging part includes a lens array having a plurality of light receiving lenses disposed like an array and is divided into an area to receive the reflected light and an area to receive transmitted light after passing through the venation, a near-infrared light irradiation source provided at an edge on a side of the area to receive the reflected light of the lens array to irradiate the finger surface with near-infrared light, and an imaging device for generating an image picking up a portion of the fingerprints based on the reflected light and generating an image picking up a portion of the venation based on the transmitted light.

A focus position of the light receiving lens positioned in an area where the reflected light is received may be set at a position of the finger surface, and the focus position of the light receiving lens positioned in an area where the transmitted light is received may be set at a position of the venation.

The vein authentication device may further include an imaging control part for controlling the imaging part, wherein the imaging control part switches irradiation of the near-infrared light emitted from the near-infrared light irradiation source between irradiation to acquire a image picking up a portion of the fingerprints and irradiation to acquire a image picking up a portion of the venation.

The near-infrared light irradiation source is constructed from a light source part for emitting the near-infrared light and a prism part for changing an optical path of the near-infrared light emitted from the light source part, and the imaging control part may control directivity of the near-infrared light emitted from the near-infrared light irradiation source by controlling the prism part.

The near-infrared light irradiation source includes a light source for acquiring an image picking up a portion of the fingerprints and a light source for acquiring an image picking up a portion of the venation, and the imaging control part may control irradiation of the near-infrared light by switching the light source used for irradiation.

The authentication part may perform, in addition to authentication processing based on the vein pattern, authentication processing based on the image of the fingerprints synthesized by the image synthesis part.

According to another embodiment of the present invention, there is provided a vein authentication method of performing authentication based on a vein pattern of venation positioned inside a finger by irradiating a finger surface with near-infrared light, including the steps of: imaging a portion of the finger surface continuously by an imaging part including a lens array having a plurality of light receiving lenses disposed like an array and is divided into an area to receive the reflected light and an area to receive transmitted light after passing through the venation, a near-infrared light irradiation source provided at an edge on a side of the area to receive the reflected light of the lens array to irradiate the finger surface with near-infrared light, and an imaging device for generating an image picking up a portion of the fingerprints based on the reflected light and generating an image picking up a portion of the venation based on the transmitted light; detecting a motion vector of the fingerprints based on a plurality of images picking up a portion of the fingerprints; synthesizing images picking up a portion of the fingerprints based on the motion vector of the fingerprints to generate an image of the fingerprints and synthesizing images picking up a portion of the venation based on the motion vector of the fingerprints to generate an image of the venation; extracting a vein pattern from the image of the venation; and performing authentication processing based on the extracted vein pattern.

According to another embodiment of the present invention, there is provided a program for causing a computer to realize an imaging part control function to control an imaging part for continuously imaging a portion of venation present inside a finger by near-infrared light scattered inside the finger by irradiating a finger surface with the near-infrared light while continuously imaging a portion of fingerprints present on the finger surface or inside the finger by reflected light reflected on the finger surface or inside the finger, a motion vector detection function to detect a motion vector of the fingerprints based on a plurality of images picking up a portion of the fingerprints, an image synthesis function to synthesize images picking up a portion of the fingerprints based on the motion vector of the fingerprints to generate an image of the fingerprints and to synthesize images picking up a portion of the venation based on the motion vector of the fingerprints to generate an image of the venation, a vein pattern extraction function to extract a vein pattern from the image of the venation, and an authentication function to perform authentication processing based on the extracted vein pattern.

According to such a configuration, a computer program is stored in a storage part provided with a computer and the computer is caused to function as the vein authentication device after the computer program being read and executed by a CPU provided with the computer. Also, a recording medium recording the computer program and readable by the computer can be provided. The recording medium is, for example, a magnetic disk, optical disk, magneto-optical disk, or flash memory. The computer program may also be delivered, for example, via a network without using any recording medium.

According to the embodiments of the present invention described above, miniaturization of a device is promoted and a wide-ranging vein image can be picked up.

DETAILED DESCRIPTION OF THE PREFERRED EMBODIMENTS

Figure 1:
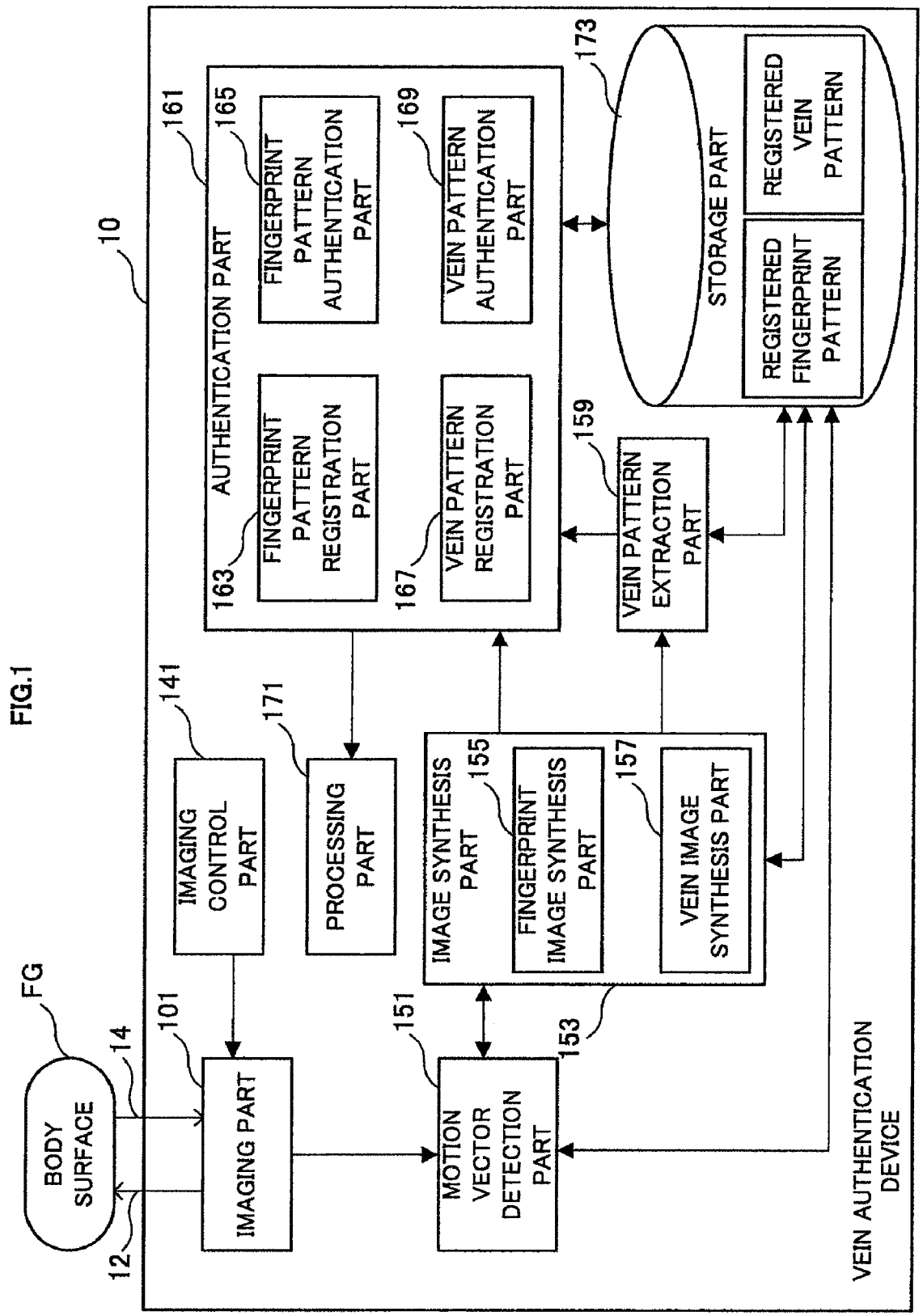
FIG. 1 is a block diagram for explaining the configuration of a vein authentication device according to a first embodiment of the present invention.

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

The inventors of the present application conceived an idea described below after due consideration to solve the above issues. That is, while a surface sensor such as a CCD (Charge Coupled Devices) and CMOS (Complementary Metal Oxide Semiconductor) is used as an image sensor for vein authentication, S/N degradation arising from thermal noise becomes an issue for such a surface sensor. Thus, it is necessary to limit the amount of light to be irradiated to a certain range to reduce such thermal noise and power consumption and to minimize an influence on human body. Moreover, it is necessary to control illumination precisely because the surface sensor easily reaches saturated luminance for some people.

However, an issue of costs or device scale arises when control described above is to be exercised, producing an issue of difficulty of miniaturizing devices.

The sensor size of a surface sensor increases when a contact device is realized, producing an issue of costs or device scale. Thus, it is necessary to adopt a system capable of suppressing costs or device scale.

Thus, as a result of intensive research to solve these issues, the inventors of the present application conceived a vein authentication device and a vein authentication method according to the present invention as described below.

First Embodiment

Configuration of Vein Authentication Device 10

First, the configuration of the vein authentication device 10 according to the first embodiment of the present invention will be described in detail with reference to FIG. 1. FIG. 1 is a block diagram for explaining the configuration of the vein authentication device 10 according to the present embodiment.

The vein authentication device 10 according to the present embodiment mainly includes, as shown, for example, in FIG. 1, an imaging part 101, an imaging control part 141, a motion vector detection part 151, an image synthesis part 153, a vein pattern extraction part 159, an authentication part 161, a processing part 171, and a storage part 173.

The imaging part 101 generates image pick-up data by imaging a body surface (for example, finger FG) of an individual who desires registration or authentication of his (her)

vein pattern. The imaging part 101 according to the present embodiment is the contact imaging part 101 using a micro lens array (MLA), which is an example of a lens array, and continuously images a portion of fingerprint and a portion of venation by irradiating placed finger FG with near-infrared light 12 of a predetermined wavelength and collecting reflected light reflected on the surface of or inside the finger FG and transmitted light 14 that passed through a vein after being scattered inside the finger FG. The imaging part 101 will be described in detail later again. In a description that follows, "an image in which a portion of fingerprint is picked up" will be abbreviated as "a fingerprint portion image" and "an image in which a portion of venation is picked up" will be abbreviated as "a venation portion image".

The imaging part 101 is drive-controlled by the imaging control part 141 including a CPU (Central Processing Unit), a ROM (Read Only Memory), and a RAM (Random Access Memory) and the imaging control part 141 outputs the obtained image pick-up data to the motion vector detection part 151 described later. The imaging control part 141 exercises control, for example, to switch irradiation of near-infrared light emitted from a near-infrared light irradiation source between irradiation to acquire a fingerprint portion image and irradiation to acquire a venation portion image. The imaging control part 141 may also record the obtained image pick-up data on the fingerprint and venation in the storage part 173. When recording such data in the storage part 173, the imaging control part 141 may associate generated image pick-up data with an imaging date or imaging time. Image pick-up data to be generated may be an RGB (Red-Green-Blue) signal or image data of other colors or gray scales.

(Configuration of imaging part 101)

Figure 2:
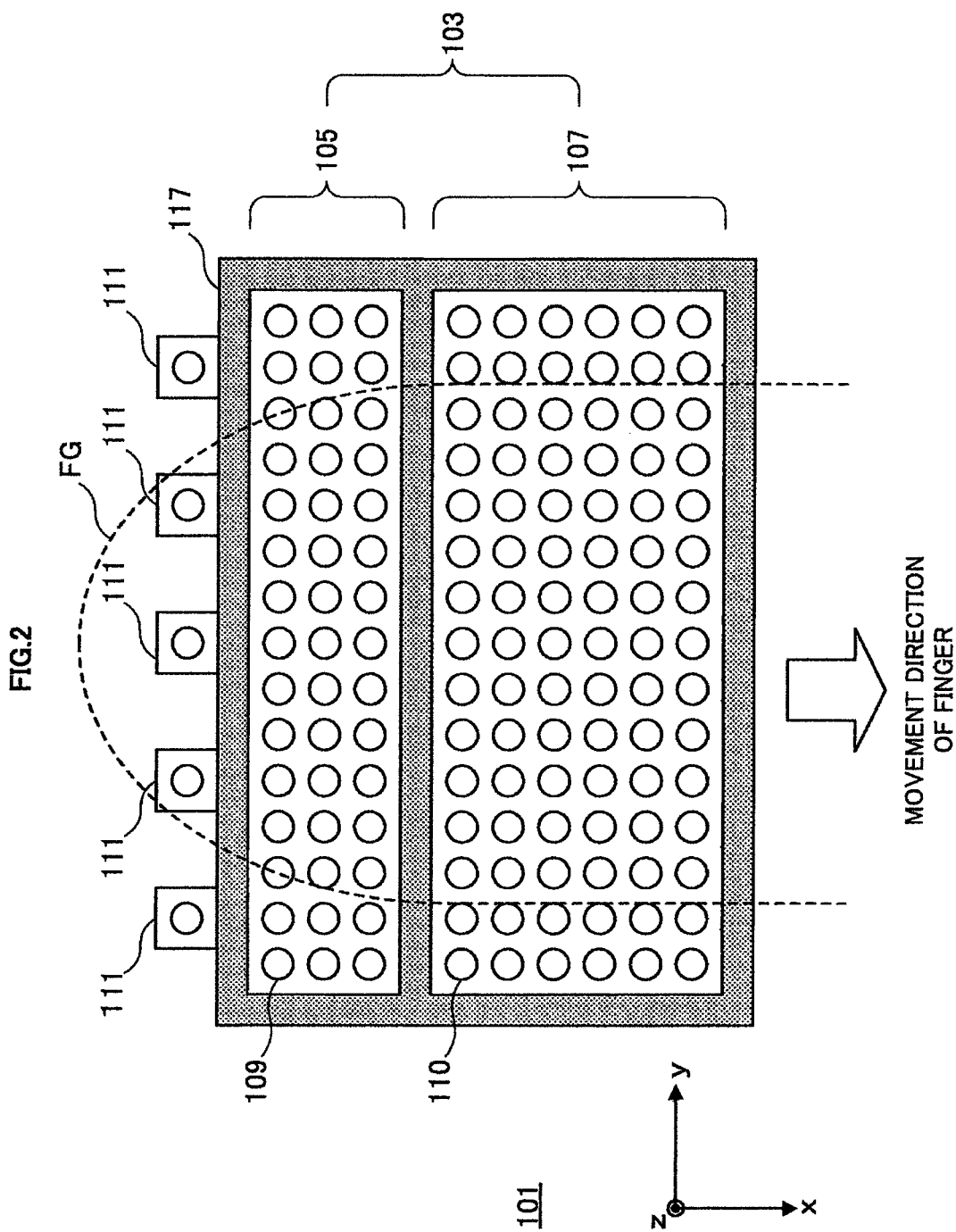
FIG. 2 is an explanatory view for explaining an imaging part according to the first embodiment.
Figure 3:
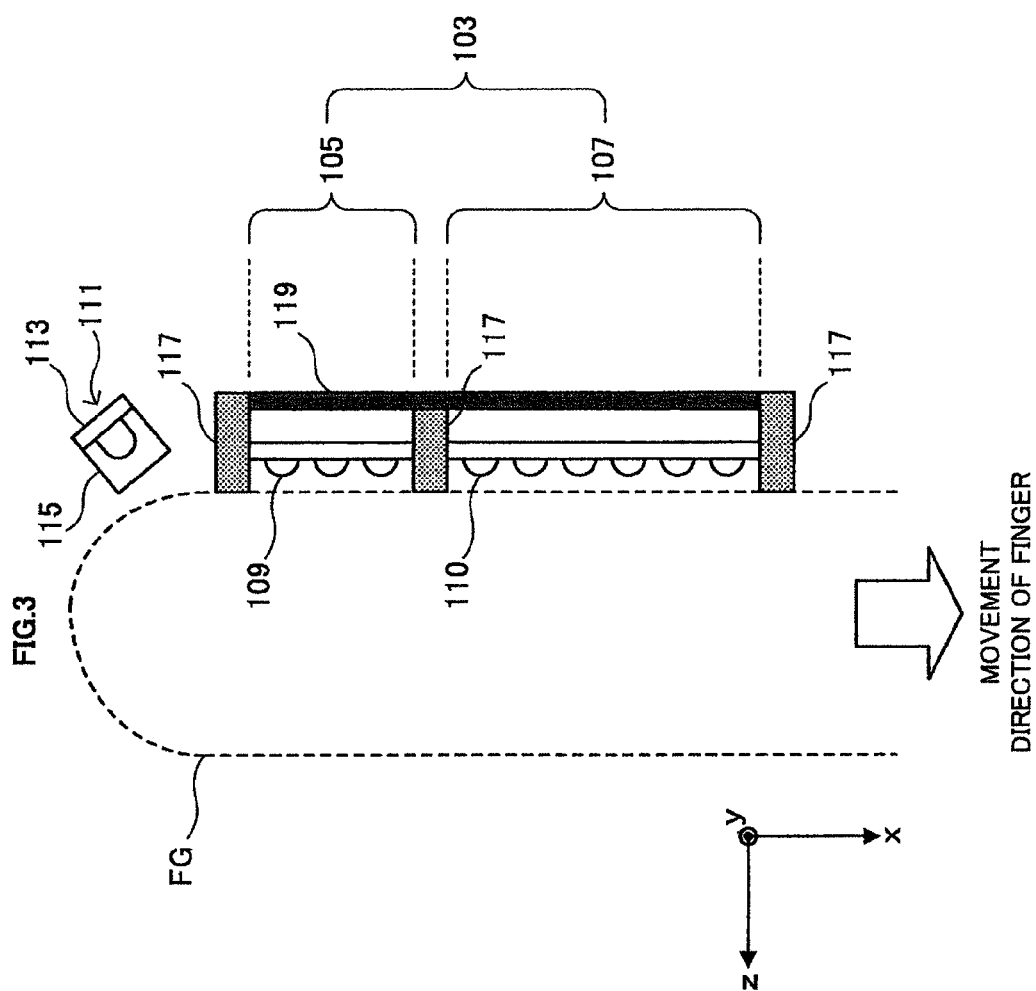
FIG. 3 is a side view for explaining the imaging part according to the first embodiment.
Figure 4:
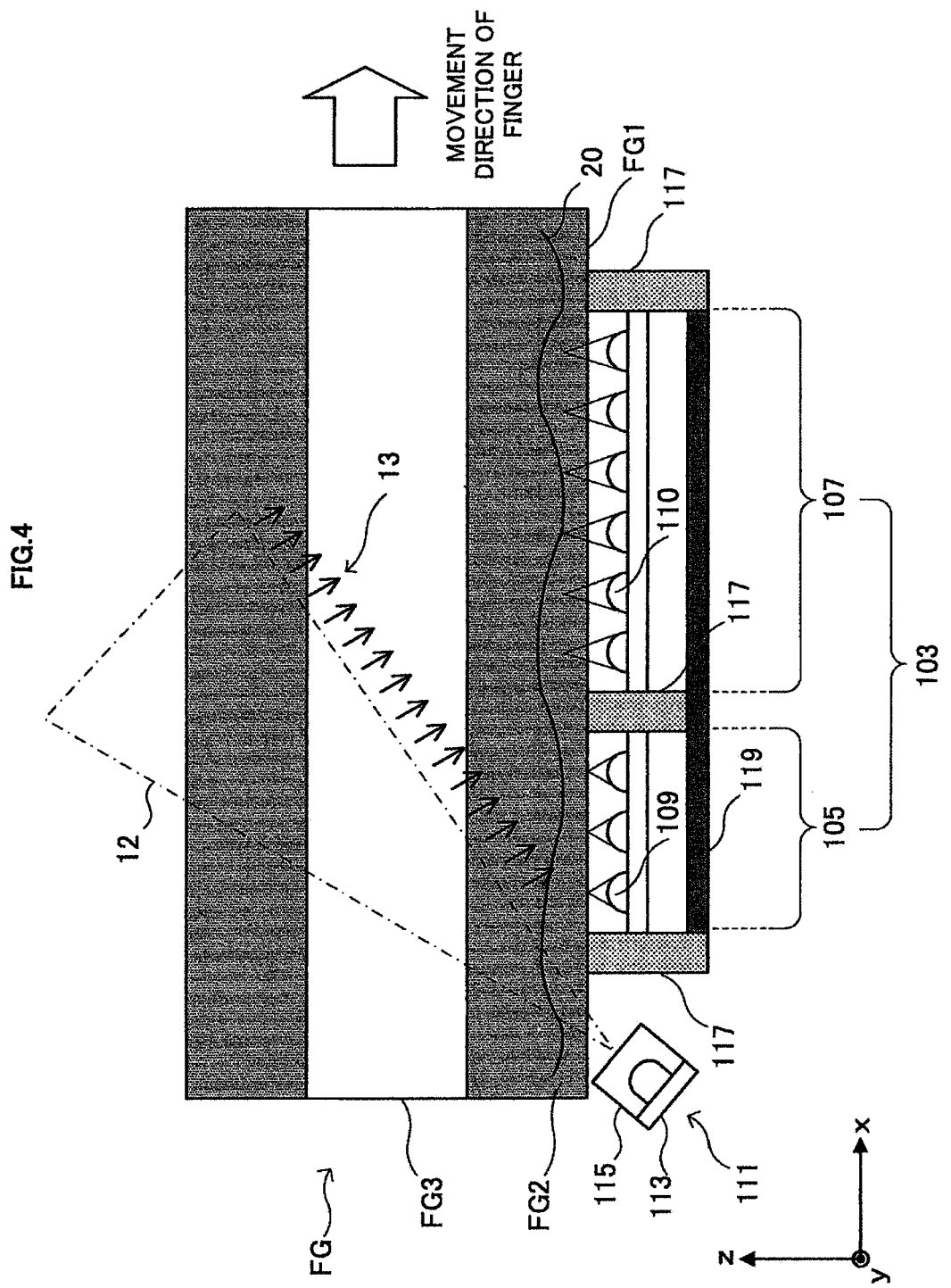
FIG. 4 is a side view for explaining the imaging part according to the first embodiment.
Figure 5:
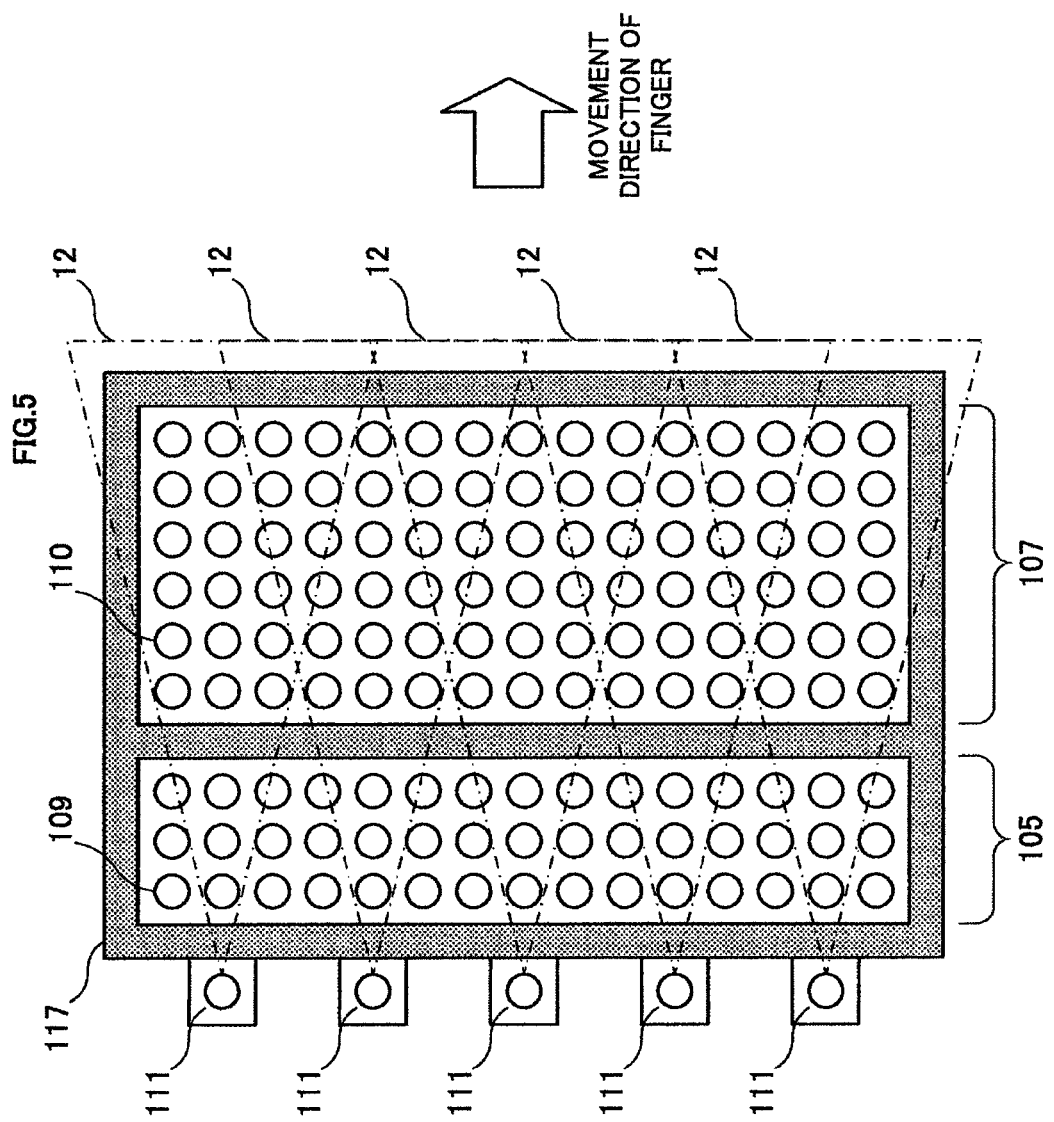
FIG. 5 is a plan view for explaining the imaging part according to the first embodiment.

Here, the configuration of the imaging part 101 provided in the vein authentication device 10 according to the present embodiment will be described in detail with reference to FIG. 2 to FIG. 5. FIG. 2 is an explanatory view for explaining the imaging part 101 according to the present embodiment. FIG. 3 and FIG. 4 are side views for explaining the imaging part 101 according to the present embodiment. FIG. 5 is a plan view for explaining the imaging part 101 according to the present embodiment.

The imaging part 101 according to the present embodiment mainly includes, as shown, for example, in FIG. 2 and FIG. 3, a micro lens array 103, which is an example of a lens array, a light emitting diode (LED) 111, which is an example of a near-infrared light irradiation source, a shading wall 117, and an imaging device 119.

The micro lens array 103 includes a plurality of micro lenses 109, 110 and is divided into two portions of a fingerprint imaging portion 105 for imaging fingerprint portion images and a venation imaging portion 107 for imaging venation portion images. As shown, for example, in FIG. 2 and FIG. 3, the plurality of micro lenses 109 is arranged in grid-like fashion in the fingerprint imaging portion 105 of the micro lens array 103 and the plurality of micro lenses 110 is arranged in grid-like fashion in the venation imaging portion 107. These micro lenses 109, 110 are arranged in grid-like fashion on a predetermined substrate. As shown, for example, in FIG. 4, each of the micro lenses 109, 110 guides reflected light and the transmitted light 14 incident on the micro lenses 109, 110 from a light incidence surface to the imaging device 119 described later. The micro lens array 103 is a lens array in which an image surface curvature is gentle and there is no distortion in the depth direction and therefore, excellent image data can be obtained by using the micro lens array 103.

The focus position of the micro lenses 109 is set to be a position of a surface skin where a fingerprint to be imaged by the fingerprint imaging portion 105 is present, and the focus position of the micro lenses 110 is set to be a position of venation where a vein to be imaged by the venation imaging portion 107 is present.

It is known that the skin of a human body has a three-layer structure of hypodermal tissue including a surface skin FG1, a corium FG2, and a bone FG3, and the venation is present in the corium FG2. The corium is a layer present with a thickness of about 2 mm to 3 mm from the position of 0.1 mm to 0.3 mm from the surface of a finger. Therefore, transmitted light that has passed through the venation can efficiently be collected by setting the focus position of the micro lens 110 to the position where such a corium is present (for example, the position of about 1.5 mm to 2.0 mm from the surface of a finger). It is also known that fingerprints are present in the surface skin FG1 and, on the other hand, 60% to 70% of the amount of irradiated near-infrared light is reflected by the surface skin FG1. Thus, reflected light reflected by the surface skin FG1 (that is, fingerprints) can efficiently be collected by setting the focus position of the micro lens 109 to the position of the surface skin FG1. Incidentally, patterns of the corium FG2 positioned near the surface skin FG1 are also known to be usable as fingerprints. In a description that follows, fingerprints present in the surface skin and patterns in the corium will together be called fingerprints.

A plurality of the light emitting diodes 111, which are an example of a near-infrared light irradiation source, is arranged, as shown, for example, in FIG. 2, outside the micro lens array 103 (more specifically, at an edge on the side of the fingerprint imaging portion 105 of the micro lens array 103) to irradiate the finger FG with near-infrared light having a predetermined wavelength band. Near-infrared light is absorbed by hemoglobin (reduced hemoglobin) in the blood while having high penetrability with respect to the system of a body and therefore, if a finger, the palm of a hand, or the back of a hand is irradiated with near-infrared light, veins distributed inside a finger, the palm of a hand, or the back of a hand appear as shadows in an image. Shadows of veins appearing in an image are called a vein pattern. To image such a vein pattern satisfactorily, a light emitting diode shines near-infrared light having wavelengths of about 600 nm to 1300 nm, preferably wavelengths of about 700 nm to 900 nm.

Here, if the wavelength of near-infrared light irradiated by the light emitting diode is less than 600 nm or more than 1300 nm, the ratio of near-infrared light absorbed by hemoglobin in the blood decreases and thus, it becomes difficult to obtain an excellent vein pattern. If the wavelength of near-infrared light irradiated by the light emitting diode is about 700 nm to 900 nm, near-infrared light is specifically absorbed by both deoxygenated hemoglobin and oxygenated hemoglobin and thus, an excellent vein pattern can be obtained.

Instead of using a light emitting diode having the wavelength band described above, a combination of a light emitting diode capable of emitting light including the wavelength band described above and a filter that optically limits emitted light in the band may be used.

The light emitting diode 111 according to the present embodiment includes, as shown, for example, in FIG. 3 and FIG. 4, a light source part 113 of the light emitting diode and a prism part 115 for changing an optical path of light emission emitted from the light source part. The prism part 115 is constructed, for example, from a prism array and controls directivity of light by changing the optical path of light emission emitted from the light source part 113. In the vein authentication device 10 according to the present embodiment, ON/OFF of the light emitting diode 111 and directivity of light emission can optionally be controlled by the light source part 113 and the prism part 115 of the light emitting diode 111 being controlled by the imaging control part 141.

Much of near-infrared light in a living body is reflected by the surface skin or corium, as described above, and thus, fingerprints and patterns of the corium can be acquired by using the reflected light. However, it is difficult to obtain clear images of veins present further deeper than the corium due to an influence of the reflected light.

With the imaging part 101 according to the present embodiment, as shown, for example, in FIG. 4 and FIG. 5, it becomes possible to realize image pick-up of surface skins and coria by reflected light and venation by backscattered light by providing the light emitting diode 111 at an edge on the fingerprint imaging portion 105 side of the micro lens array 103.

Near-infrared light emitted from the light emitting diode 111 propagates, as shown, for example, in FIG. 4, toward the surface (surface skin) FG1 of the finger FG and a portion thereof enters the micro lenses 109 as reflected light after being reflected by the surface skin FG1. Also, a portion of near-infrared light emitted from the light emitting diode 111 enters the finger FG as direct light 12. Here, a human body is an excellent scatterer of near-infrared light and thus, the direct light 12 that enters the finger FG propagates while being scattered in all directions. A portion of the scattered light transmits from the back of venation 20 toward the finger surface as backscattered light 13 before entering the micro lenses 109 as the transmitted light 14.

The contrast ratio in a minimum area can be made optimal by light source scanning of the light emitting diode 111 being controlled by the imaging control part 141. For example, the light source part 113 arranged below the prism part 115 of the light emitting diode 111 is driven by the imaging control part 141 by being associated with a scanning signal of the imaging part 101. If the light source part 113 is lit, as shown, for example, in FIG. 5, illumination of a predetermined area is executed by the prism part 115 arranged above the light source part 113. At this point, if the prism part 115 and an imaging line are sufficiently apart, the backscattered light 13 of veins by the incident direct light 12 can efficiently be extracted so that a vein image of high contrast ratio can be obtained. By blinking each of the light emitting diodes 111 together with scan lines, as shown, for example, in FIG. 5, illumination mostly satisfying imaging conditions can be achieved.

Further, by using cross correlations by the time axis for image pick-up of fingerprints and image pick-up of venation, stabilization of each evaluation can be realized. Moreover, with reliable settings being executable, stability of authentication precision and the device can be realized.

The above description uses a case in which a single light emitting diode array is used, but two light emitting diode arrays may also be used for irradiation of near-infrared light. That is, a light emitting diode array used for imaging fingerprint portion images is arranged at an edge on the fingerprint imaging portion 105 side of the micro lens array 103 and that for imaging venation portion images is arranged at an edge on the venation imaging portion 107 side of the micro lens array 103. In this case, various settings are made for each light emitting diode array so as to achieve irradiation conditions suitable for each irradiation target and the imaging control part 141 exercises control to switch irradiation of each light emitting diode array.

Near-infrared light having the same wavelength may be used for image pick-up of fingerprints and image pick-up of venation, or near-infrared light having different wavelengths may be used for image pick-up of fingerprints and image pick-up of venation.

Here, as shown, for example, in FIG. 2 to FIG. 4, the shading wall 117 is provided between the micro lens array 103 and the light emitting diodes 111 and between the fingerprint imaging portion 105 and the venation imaging portion 107. The shading wall 117 shades the direct light 12 so that the direct light 12 emitted from the light emitting diodes 111 does not directly enter the micro lenses 109, 110.

The imaging device 119 has an imaging surface in which a plurality of imaging devices is arranged in grid-like fashion and generates image pick-up data by near-infrared light based on reflected light and the transmitted light 14 collected by the micro lenses 109, 110. For example, a CCD type image sensor, a C-MOS type image sensor or the like may be used as the imaging device 119 according to the present embodiment. The imaging device 119 outputs the generated image pick-up data to the motion vector detection part 151 described later. The imaging device 119 may also store the generated image pick-up data in the storage part 173 described later.

In the imaging part 101 according to the present embodiment, a filter to limit the optical band suitable for vein image pick-up for light (the transmitted light 14) that passed through venation to be measured may further be provided between the finger FG and the imaging device 113.

The configuration of the imaging part 101 according to the present embodiment has been described above with reference to FIG. 2 to FIG. 4. The configuration of the vein authentication device 10 according to the present embodiment will be described below further with reference to FIG. 1.

The motion vector detection part 151 includes, for example, a CPU, ROM, RAM and the like and analyzes a plurality of fingerprint portion images generated by the imaging part 101 to detect a motion vector of fingerprints. A motion vector of fingerprints can be detected, for example, by a method described below. Fingerprint portion images generated by the imaging part 101 are images of an uplifted portion (in other words, a peak portion) of uneven fingerprints present in the surface skin or corium. Thus, first a fingerprint portion image is focused on and the distance between adjacent peaks (or the distance between adjacent valleys) is calculated. Subsequently, the distance between peaks or the distance between valleys in another fingerprint portion image is similarly calculated. By analyzing the plurality of obtained fingerprint portion images by focusing on the distance between peaks, a motion vector of fingerprints can be detected.

In addition to the detection method of a motion vector described above, for example, a detection method of a motion vector used in fingerprint authentication technology can be used.

The motion vector detection part 151 outputs the motion vector of fingerprints detected in this manner to the image synthesis part 153 described later. The motion vector detection part 151 may also store the detected motion vector in the storage part 173 described later.

The image synthesis part 153 includes, for example, a CPU, ROM, RAM and the like and synthesizes a fingerprint image and a vein image based on a motion vector detected by the motion vector detection part 151. The image synthesis part 153 further includes a fingerprint image synthesis part 155 and a vein image synthesis part 157.

The fingerprint image synthesis part 155 generates an image of fingerprints by synthesizing a plurality of fingerprint portion images transmitted from the imaging part 101 based on motion vectors transmitted from the motion vector detection part 151. If fingerprint portion images transmitted from the imaging part 101 are mirror images when images are synthesized, the fingerprint image synthesis part 155 may perform reversal processing of each fingerprint portion image before performing synthesis processing. If it is necessary to perform correction processing such as aberration corrections and corrections of brightness distribution on fingerprint portion images transmitted from the imaging part 101, the fingerprint image synthesis part 155 may perform various kinds of correction processing on fingerprint portion images before synthesis or picked-up images after synthesis.

The fingerprint image synthesis part 155 outputs a synthesized image of fingerprints to the authentication part 161 described later as a fingerprint pattern. The fingerprint image synthesis part 155 may also store the synthesized image of fingerprints in the storage part 173 described later.

The vein image synthesis part 157 generates a venation image by synthesizing a plurality of venation portion images transmitted from the imaging part 101 based on motion vectors transmitted from the motion vector detection part 151. If venation portion images transmitted from the imaging part 101 are mirror images when images are synthesized, the vein image synthesis part 157 may perform reversal processing of each venation portion image before performing synthesis processing. If it is necessary to perform correction processing such as aberration corrections and corrections of brightness distribution on venation portion images transmitted from the imaging part 101, the vein image synthesis part 157 may perform various kinds of correction processing on venation portion images before synthesis or picked-up images after synthesis.

The vein image synthesis part 157 outputs a synthesized image of venation to the vein pattern extraction part 159 described later. The vein image synthesis part 157 may also store the synthesized image of venation in the storage part 173 described later.

The vein pattern extraction part 159 includes, for example, a CPU, ROM, RAM and the like and has, for example, a function to perform preprocessing of vein pattern extraction from image pick-up data of venation transmitted from the vein image synthesis part 157, a function to extract a vein pattern, and a function to perform post-processing of vein pattern extraction.

Here, the preprocessing of vein pattern extraction includes, for example, processing to detect outlines of fingers from image pick-up data of venation to identify at which position of image pick-up data of venation fingers are located and processing to correct the angle of image pick-up data of venation (angle of images) by rotating the image data using the detected outlines of fingers.

The extraction of a vein pattern is achieved by applying a differential filter to image pick-up data of venation in which outlines have been detected and angle corrections have been made. The differential filter is a filter that focuses on a pixel together with neighboring pixels and outputs a large value as an output value in portions where a difference between the focused pixel and neighboring pixels is large. In other words, the differential filter is a filter to emphasize lines or edges in an image based on operations using a difference of gradation values between the focused pixel and neighboring pixels.

If filter processing is performed using a filter h (x, y) on image data u (x, y) having a lattice point (x, y) in a two-dimensional plane as variables, as shown in the following formula 1, image data v (x, y) is generally generated. Here, "*" in the following formula 1 indicates a convolution.

$$v(x, y) = u(x, y) * h(x, y) \quad \text{[Formula 1]}$$
$$= \sum_{m_1} \sum_{m_2} h(m_1, m_2) u(x, -m_1, y - m_2)$$
$$= \sum_{m_1} \sum_{m_2} u(m_1, m_2) h(x, -m_1, y - m_2)$$

In the extraction of a vein pattern according to the present embodiment, a differentiation filter such as a one-dimensional space differentiation filter and a two-dimensional space differentiation filter may be used as the differential filter. The one-dimensional space differentiation filter is a filter that calculates a difference of gradations values of adjacent pixels in the horizontal direction and the vertical direction regarding the focused pixel, and the two-dimensional space differentiation filter is a filter to extract portions where the amount of change of a difference of gradations values regarding the focused pixel increases.

A Log (Laplacian of Gaussian) filter shown below, for example, can be used as the two-dimensional space differentiation filter. The Log filter (formula 3) is represented as secondary differentiation of a Gaussian filter (formula 2), which is a smoothing filter using a Gaussian function. Here, σ represents the standard deviation of the Gaussian function in the following formula 2 and is a variable representing the degree of smoothing of the Gaussian filter. σ in the following formula 3 is a parameter representing, like the formula 2, the standard deviation of the Gaussian function and can change the output value when Log filter processing is performed by changing the value of σ.

$$h_{gauss}(x, y) = \frac{1}{2\pi\sigma^2} \exp\left\{-\frac{(x^2 + y^2)}{2\sigma^2}\right\} \quad \text{(Formula 2)}$$

$$h_{Log}(x, y) = \nabla^2 \cdot h_{gauss}(x, y) \quad \text{(Formula 3)}$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6} \exp\left\{-\frac{(x^2 + y^2)}{2\sigma^2}\right\}$$

The post-processing of vein pattern extraction includes, for example, threshold processing, binarization processing, and thinning processing performed on image data after differential filter application. A skeleton of vein patterns can be extracted after undergoing the post-processing.

The vein pattern extraction part 159 transmits vein patterns and skeletons extracted in this manner to the authentication part 161 described later. The vein pattern extraction part 159 may also store the extracted vein patterns and skeletons in the storage part 173 described later. When performing each piece of the above processing, the vein pattern extraction part 159 may store generated parameters, progress of processing and the like in the storage part 173.

The authentication part 161 includes, for example, a CPU, ROM, RAM and the like and registers a vein pattern generated by the vein pattern extraction part 159 as a template and performs authentication of a vein pattern by checking the vein pattern generated by the vein pattern extraction part 159 against templates already registered. Moreover, the authentication part 161 registers a fingerprint pattern generated by the fingerprint image synthesis part 155 as a template and performs authentication of a fingerprint pattern by checking the fingerprint pattern generated by the fingerprint image synthesis part 155 against templates already registered. The authentication part 161 further includes, for example, a fingerprint pattern registration part 163, a fingerprint pattern authentication part 165, a vein pattern registration part 167, and a vein pattern authentication part 169.

The fingerprint pattern registration part 163 registers a fingerprint pattern generated by the fingerprint image synthesis part 155 as a template. When registering a registered fingerprint pattern, not only the fingerprint pattern, but also other data (for example, vein data, face image data, iris data, and voice print data) identifying an individual having the fingerprint pattern may be stored by associating with the fingerprint pattern. A registered fingerprint pattern to be registered as a template may have header information conforming, for example, to the standard of CBEFF (Common Biometric Exchange File Format) or the like.

The fingerprint pattern authentication part 165 performs authentication of a generated fingerprint pattern based on the fingerprint pattern generated by the fingerprint image synthesis part 155 and templates of recorded fingerprint patterns. The fingerprint pattern authentication part 165 requests a disclosure of registered fingerprint patterns from the storage part 173 described later and compares the acquired registered fingerprint patterns and a fingerprint pattern transmitted from the fingerprint image synthesis part 155. A registered fingerprint pattern and a transmitted fingerprint pattern can be compared, for example, by calculating a correlation coefficient shown below to make a comparison based on the calculated correlation coefficient. If, as a result of comparison, the registered fingerprint pattern and the transmitted fingerprint pattern are similar, the fingerprint pattern authentication part 165 performs authentication of the transmitted fingerprint pattern and, if both patterns are not similar, the fingerprint pattern authentication part 165 does not perform authentication.

The vein pattern registration part 167 registers a vein pattern generated by the vein pattern extraction part 159 in the storage part 173 described later as a template. When registering a registered vein pattern, not only the vein pattern, but also other data (for example, fingerprint data, face image data, iris data, and voice print data) identifying an individual having the vein pattern may be stored by associating with the vein pattern. A registered vein pattern to be registered as a template may have header information conforming, for example, to the standard of CBEFF (Common Biometric Exchange File Format) or the like.

The vein pattern authentication part 169 performs authentication of a generated vein pattern based on the vein pattern generated by the vein pattern extraction part 159 and templates of recorded vein patterns. The vein pattern authentication part 169 requests a disclosure of registered vein patterns from the storage part 173 described later and compares the acquired registered vein patterns and a vein pattern transmitted from the vein pattern extraction part 159. A registered vein pattern and a transmitted vein pattern can be compared, for example, by calculating a correlation coefficient shown below to make a comparison based on the calculated correlation coefficient. If, as a result of comparison, the registered vein pattern and the transmitted vein pattern are similar, the vein pattern authentication part 169 performs authentication of the transmitted vein pattern and, if both patterns are not similar, the vein pattern authentication part 169 does not perform authentication.

The correlation coefficient is defined by the following formula 4, is a statistical index showing similarities between two pieces of data $x=\{x_i\}$ and $y=\{y_i\}$, and takes a real number between $-1$ and $1$. When the correlation coefficient obtains a value close to 1, the two data are similar to each other, and when the correlation coefficient obtains a value close to 0, the two data are not similar. When the correlation coefficient obtains a value close to $-1$, codes of the two data are inverted.

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad \text{(Formula 4)}$$

$\bar{x}$: an average value of data x
$\bar{y}$: an average value of data y

The fingerprint pattern authentication part 165 and the vein pattern authentication part 169 may store an authentication result in the storage part 173 as an authentication history by associating with an authentication time and the like. Generating such an authentication history enables one to know who requested authentication of a fingerprint pattern or vein pattern and when and, by extension, who used the vein authentication device 10 and when.

The processing part 171 includes, for example, a CPU, ROM, RAM and the like and performs predetermined processing in accordance with an authentication result of a vein pattern output from the authentication part 161. That is, after receiving a notification of successful authentication of a vein pattern from the authentication part 161, the processing part 171 lifts restrictions on execution of predetermined processing and performs the predetermined processing. The processing part 171 may also perform the predetermined processing in accordance with an authentication result of a fingerprint pattern, in addition to an authentication result of a vein pattern. A high security level can be realized by doubly performing authentication by a fingerprint pattern and authentication by a vein pattern.

The storage part 173 stores a registered fingerprint pattern requested to register by the fingerprint pattern registration part 163 and other data associated with the registered fingerprint pattern. The storage part 173 also stores a registered vein pattern requested to register by the vein pattern registration part 167 and other data associated with the registered vein pattern. In addition to the above data, image pick-up data generated by the imaging part 101, vein patterns extracted by the vein pattern extraction part 159 and the like can be stored. Further, in addition to the above data, various parameters that are necessary to be stored when performing certain processing and progress of processing, or various kinds of databases can be appropriately stored. The storage part 173 can freely be read or written to by the imaging part 101, the imaging control part 141, the motion vector detection part 151, the image synthesis part 153, the vein pattern extraction part 159, the authentication part 161, and the processing part 171.

An example of the function of the vein authentication device 10 according to the present embodiment has been shown above. Each of the above components may be constituted by using general-purpose members or circuits, or by hardware tailored to the function of each component. Alternatively, the function of each component may be all executed by the CPU. Therefore, the constitution to be used can be changed suitably in accordance with the technological level when the present embodiment is carried out.

The vein authentication device 10 according to the present embodiment may be implemented in various devices, for example, in an information processing device such as a computer and server, a mobile terminal such as a mobile phone and PHS or a personal digital assistant (PDA), an automatic teller machine (ATM), an access control device, and a game machine or a controller of a game machine.

The above description uses a case in which a registered vein pattern to be registered as a template is recorded in the vein authentication device 10, but the registered vein pattern may also be recorded in a recording medium such as a DVD medium, HD-DVD medium, Blu-ray medium, Compact-Flash (registered trademark), memory stick, and SD memory card, or an IC card or electronic device equipped with a non-contact IC chip, or may be recorded in a server connected to the vein authentication device 10 via a network such as the Internet.

<Vein Authentication Method According to the Present Embodiment>

Figure 6:
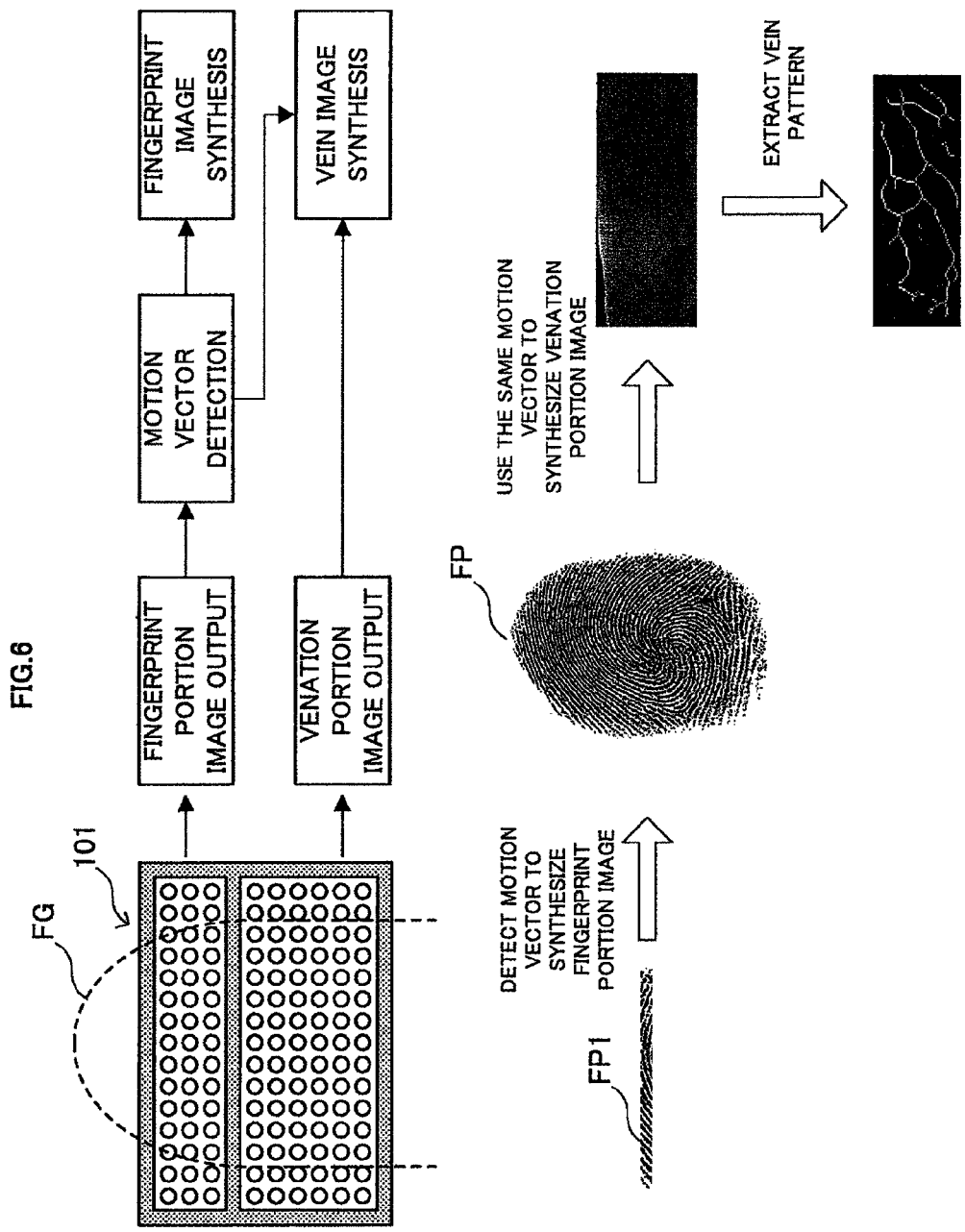
FIG. 6 is an explanatory view for explaining a vein authentication method according to the first embodiment.
Figure 7:
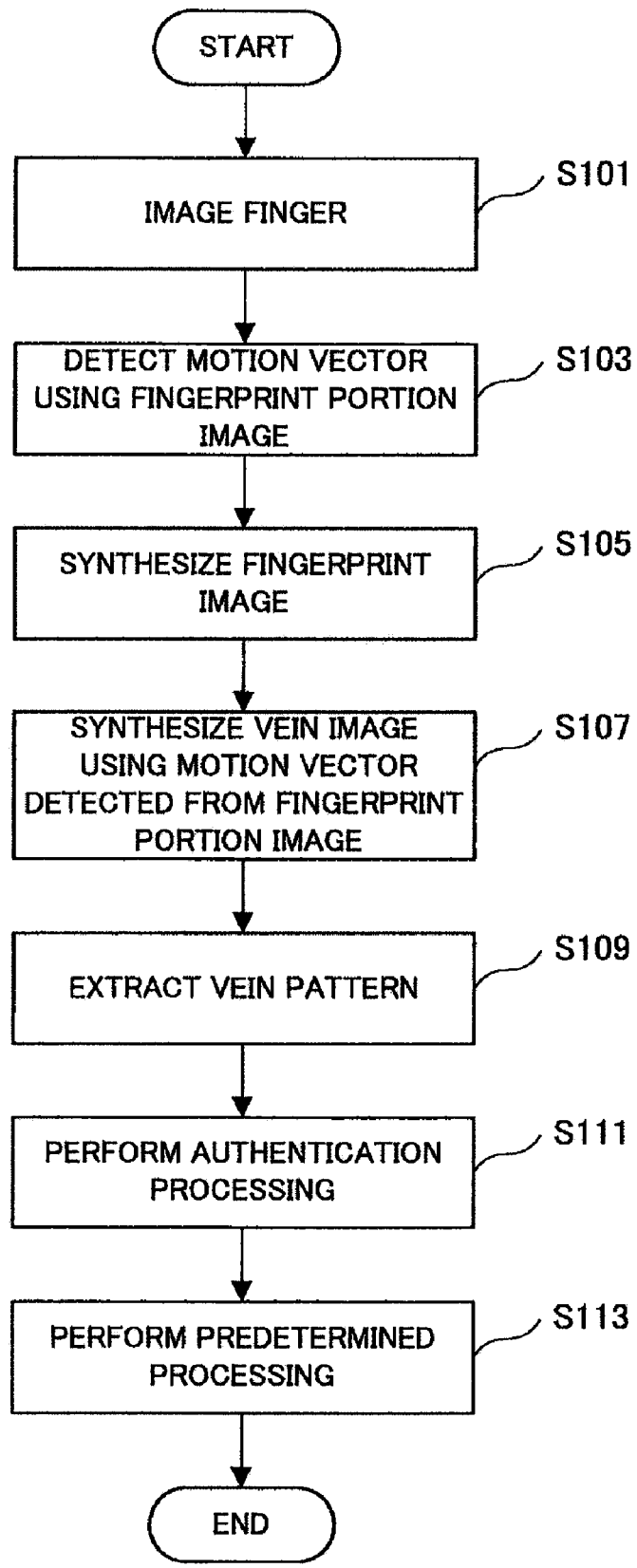
FIG. 7 is a flow chart for explaining the vein authentication method according to the first embodiment.

Next, a vein authentication method according to the present embodiment will be described in detail with reference to FIG. 6 and FIG. 7. FIG. 6 is an explanatory view for explaining a vein authentication method according to the present embodiment and FIG. 7 is a flow chart for explaining the vein authentication method according to the present embodiment.

First, the imaging part 101 of the vein authentication device 10 according to the present embodiment irradiates a finger placed in the imaging part 101 with near-infrared light to continuously take fingerprints present in the surface skin or corium and to image venation positioned inside the finger (step S101). Each piece of image pick-up data generated by the imaging part 101 is output to the motion vector detection part 151 of the vein authentication device 10 according to the present embodiment.

Next, based on a plurality of fingerprint portion images FP1 output from the imaging part 101, the motion vector detection part 151 detects a motion vector of fingerprints (step S103). After detection processing of motion vector is completed, the motion vector detection part 151 outputs detected motion vectors to the image synthesis part 153.

Subsequently, the fingerprint image synthesis part 155 of the image synthesis part 153 synthesizes the plurality of fingerprint portion images FP1 based on motion vectors output from the motion vector detection part 151 to generate an image of the fingerprints FP (step S105). After synthesis of the image of the fingerprints is completed, the fingerprint image synthesis part 155 outputs the generated image of the fingerprints to the authentication part 161 as a fingerprint pattern.

Next, the vein image synthesis part 157 of the image synthesis part 153 synthesizes a plurality of venation portion images based on motion vectors output from the motion vector detection part 151 to generate an image of the venation (step S107). After synthesis of the image of the venation is completed, the vein image synthesis part 157 outputs the generated image of the venation to the vein pattern extraction part 159.

Subsequently, the vein pattern extraction part 159 extracts a vein pattern from image pick-up data transmitted from the vein image synthesis part 157 (step S109). After extraction of the vein pattern is completed, the vein pattern extraction part 159 outputs the extracted vein pattern to the authentication part 161.

Next, based on the vein pattern output from the vein pattern extraction part 159, the authentication part 161 performs authentication processing of the vein pattern (step S111). Here, if a user who uses the vein authentication device 10 desires to register a vein pattern, the vein pattern registration part 167 of the authentication part 161 records the vein pattern output from the vein pattern extraction part 159 in the storage part 173 as a registered vein pattern. If the user who uses the vein authentication device 10 desires to authenticate a vein pattern, the vein pattern authentication part 169 of the authentication part 161 compares registered vein patterns already registered and a vein pattern output from the vein pattern extraction part 159 and if the vein pattern output from the vein pattern extraction part 159 is a registered vein pattern, notifies the processing part 171 of successful authentication. If the vein pattern output from the vein pattern extraction part 159 does not match the registered vein patterns, the authentication part 161 notifies the processing part 171 of failed authentication.

In addition to the registration processing and authentication processing of vein patterns, the authentication part 161 may also perform registration processing and authentication processing for fingerprint patterns transmitted from the fingerprint image synthesis part 155.

Subsequently, the processing part 171 performs predetermined processing in accordance with an authentication result notified from the authentication part 161 (step S13). That is, if a notification of successful authentication is received from the authentication part 161, the processing part 171 lifts restrictions on execution of predetermined processing and performs the predetermined processing. If a notification of failed authentication is received from the authentication part 161, the processing part 171 terminates processing.

<Hardware Configuration of Vein Authentication Device>

Figure 8:
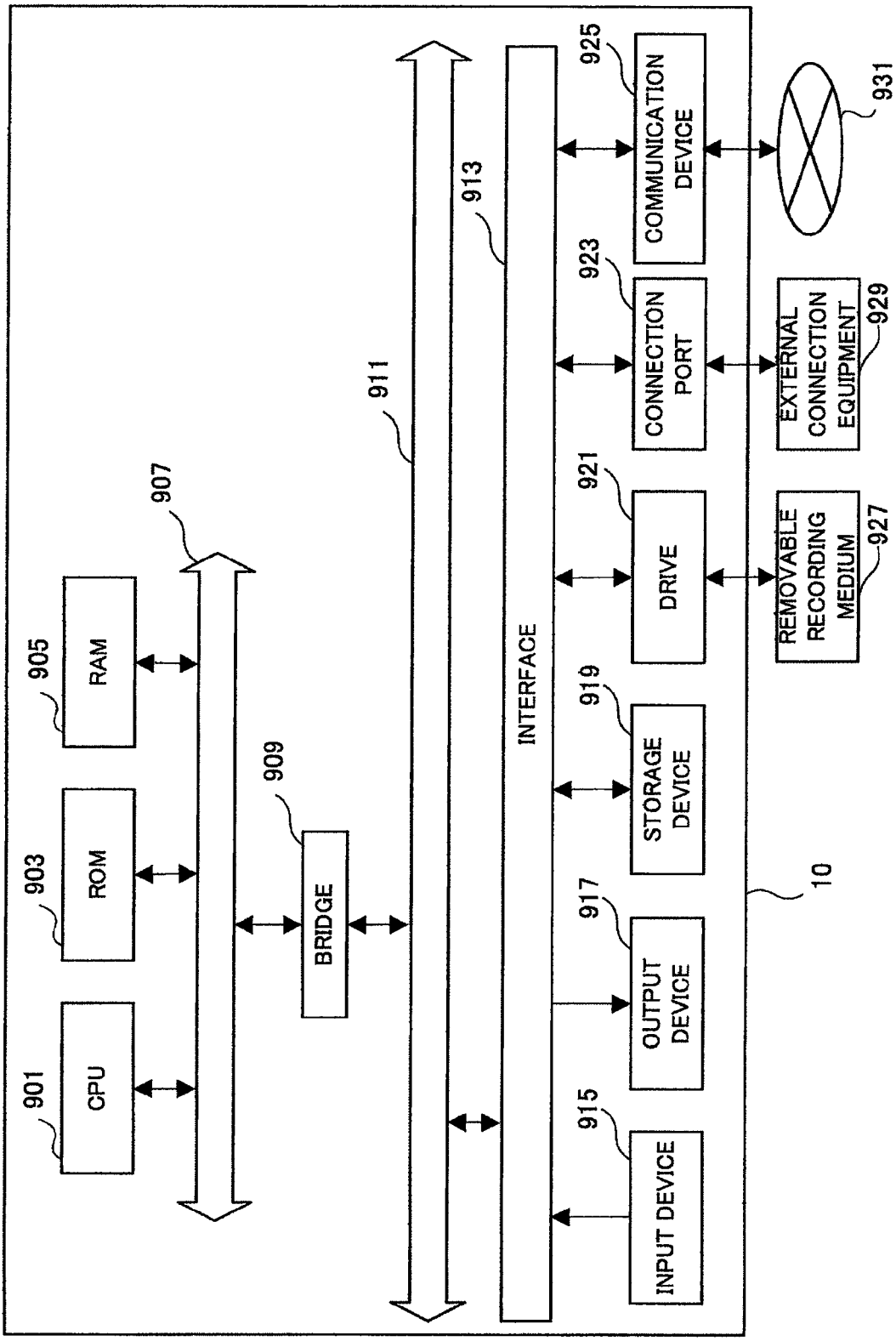
FIG. 8 is a block diagram for explaining a hardware configuration of the vein authentication device according to the first embodiment.

Next, the hardware configuration of the vein authentication device 10 according to the present embodiment will be described in detail with reference to FIG. 8. FIG. 8 is a block diagram for explaining the hardware configuration of the vein authentication device 10 according to the present embodiment.

The vein authentication device 10 mainly includes a CPU 901, a ROM 903, a RAM 905, a host bus 907, a bridge 909, an external bus 911, an interface 913, an input device 915, an output device 917, a storage device 919, a drive 921, a connection port 923, and a communication device 925.

The CPU 901 functions as a processor and control device and controls overall operations in the vein authentication device 10 or a portion thereof in accordance with various programs recorded in the ROM 903, the RAM 905, the storage device 919, or a removable recording medium 927. The ROM 903 stores programs, operation parameters and the like used by the CPU 901. The RAM 905 is used as a primary memory of programs used for execution of the CPU 901 and parameters that change suitably in execution thereof. These components are mutually connected by the host bus 907 constructed from an internal bus such as a CPU bus.

The host bus 907 is connected to the external bus 911 such as a PCI (Peripheral Component Interconnect/Interface) bus via the bridge 909.

The input device 915 is an operation unit operated by a user such as mouse, keyboard, touch panel, button, switch, and lever. The input device 915 may also be, for example, a remote control unit (a so-called remote control) using infrared rays or other electric waves or an external connection device 929 such as a mobile phone and PDA in accordance with operations of the vein authentication device 10. Further, the input device 915 generates an input signal, for example, based on information input by a user using the operation unit and includes an input control circuit for output to the CPU 901. The user of the vein authentication device 10 can input various kinds of data into the vein authentication device 10 and instruct processing operations by operating the input device 915.

The output device 917 is constructed from a device capable of visually or acoustically notifying a user of acquired information, for example, from a display device such as a CRT display device, liquid crystal display device, plasma display device, EL display device, and lamp, a sound output device such as a speaker and headphone, a printer, a mobile phone, or a facsimile. The output device 917 outputs, for example, results obtained from various kinds of processing performed by the vein authentication device 10. More specifically, the display device displays results obtained from various kinds of processing performed by the vein authentication device 10 as text or images. The sound output device, on the other hand, converts an audio signal including reproduced sound data and acoustic data into an analog signal for output.

The storage device 919 is a device for data storage constructed as an example of storage part of the vein authentication device 10 and includes, for example, a magnetic storage part device such as an HDD (Hard Disk Drive), a semiconductor storage device, an optical storage device, or a magneto-optical device. The storage device 919 stores programs executed by the CPU 901, various kinds of data, and acoustic signal data and image signal data acquired from outside.

The drive 921 is a reader/writer for recording media and is contained in the vein authentication device 10 or used as an external device. The drive 921 reads information recorded in the removable recording medium 927 such as an inserted magnetic disk, optical disk, magneto-optical disk, and semiconductor memory and outputs the information to the RAM 905. The drive 921 can also write a record into the removable recording medium 927 such as an inserted magnetic disk, optical disk, magneto-optical disk, and semiconductor memory. The removable recording medium 927 is, for example, a DVD medium, HD-DVD medium, Blu-ray medium, CompactFlash (CF) (registered trademark), memory stick, or SD memory card (Secure Digital memory card). The removable recording medium 927 may also be, for example, an IC card (Integrated Circuit card) or electronic device equipped with a non-contact IC chip.

The connection port 923 is a port for directly connecting a device to the vein authentication device 10 such as a USB (Universal Serial Bus) port, an IEEE1394 port such as an i. Link, an SCSI (Small Computer System Interface) port, an RS-232C port, an optical audio terminal, and HDMI (High-Definition Multimedia Interface) port. By connecting the external connection device 929 to the connection port 923, the vein authentication device 10 acquires acoustic signal data and image signal data directly from the external connection device 929 and provides acoustic signal data and image signal data to the external connection device 929.

The communication device 925 is a communication interface including, for example, a communication device for connecting to a communication network 931. The communication device 925 is, for example, a wire or wireless LAN (Local Area Network), a communication card for Bluetooth or WUSB (Wireless USB), a router for optical communication, a router for ADSL (Asymmetrical Digital Subscriber Line), or a modem for various kinds of communication. The communication device 925 can, for example, send and receive an acoustic signal to/from the Internet or other communication devices. The communication network 931 connected to the communication device 925 is constructed from a network or the like connected by wire or wireless, and may be, for example, the Internet, home LAN, infrared-ray communication, radio wave communication, or satellite communication.

An example of the hardware configuration capable of realizing the vein authentication device 10 according to the embodiment of the present invention has been shown above. Each of the above components may be constituted by using general-purpose members, or by hardware tailored to the function of each component. Therefore, the hardware configuration to be used can be changed appropriately in accordance with the technological level when the present embodiment is carried out.

According to the vein authentication device 10 and the vein authentication method in the present embodiment, as described above, finger vein authentication can be implemented in a planar structure by using reflected/scattered light in the planar structure and by extension, a contact vein authentication device promoting miniaturization of the device and capable of picking up a wide-ranging vein image from local image can be realized.

In a vein authentication device in related art, it is necessary to provide an angle of about 120 degrees to the near-infrared light irradiation source to ensure a sufficient contrast ratio of images for an imaging area, making the whole device to carry out the light source larger. Moreover, because a vein pattern is simple in a small area, it is difficult to calculate a motion vector with sufficient precision from the vein pattern. However, the vein authentication device 10 according to the present invention can obtain an image of a surface skin/corium and that of venation at the same time and therefore, a motion vector can be calculated from an image enabling detection of a motion vector with sufficient precision to use the calculated motion vector for synthesis of an image of the venation. Consequently, a wide-ranging vein image can be acquired from a small sensor.

It should be understood by those skilled in the art that various modifications, combinations, sub-combinations and alterations may occur depending on design requirements and other factors insofar as they are within the scope of the appended claims or the equivalents thereof.

In the above embodiment, for example, a case in which a finger is scanned in the X-axis direction in figures is described, but the same effect can be achieved when the finger is scanned in the Y-axis direction in figures.

What is claimed is:
1. A vein authentication device, comprising:
an imaging part for continuously imaging a portion of venation present inside a finger by near-infrared light scattered inside the finger by irradiating a finger surface with the near-infrared light while continuously imaging a portion of fingerprints present on the finger surface or inside the finger by reflected light reflected on the finger surface or inside the finger;
a motion vector detection part for detecting a motion vector of the fingerprints based on a plurality of images picking up a portion of the fingerprints;
an image synthesis part for synthesizing images picking up a portion of the fingerprints based on the motion vector of the fingerprints to generate an image of the fingerprints and synthesizing images picking up a portion of the venation based on the motion vector of the fingerprints to generate an image of the venation;
a vein pattern extraction part for extracting a vein pattern from the image of the venation; and an authentication part for performing authentication processing based on the extracted vein pattern, wherein
the imaging part includes:
a lens array having a plurality of light receiving lenses disposed like an array and is divided into an area to receive the reflected light and an area to receive transmitted light after passing through the venation;

a near-infrared light irradiation source provided at an edge on a side of the area to receive the reflected light of the lens array to irradiate the finger surface with near-infrared light; and an imaging device for generating an image picking up a portion of the fingerprints based on the reflected light and generating an image picking up a portion of the venation based on the transmitted light, wherein a focus position of the light receiving lens positioned in an area where the reflected light is received is set at a position of the finger surface.

2. The vein authentication device according to claim 1, wherein the focus position of the light receiving lens positioned in an area where the transmitted light is received is set at a position of the venation.

3. The vein authentication device according to claim 2, further comprising:

an imaging control part for controlling the imaging part, wherein the imaging control part switches irradiation of the near-infrared light emitted from the near-infrared light irradiation source between irradiation to acquire an image picking up a portion of the fingerprints and irradiation to acquire an image picking up a portion of the venation.

4. The vein authentication device according to claim 3, wherein the near-infrared light irradiation source is constructed from a light source part for emitting the near-infrared light and a prism part for changing an optical path of the near-infrared light emitted from the light source part, and the imaging control part controls directivity of the near-infrared light emitted from the near-infrared light irradiation source by controlling the prism part.

5. The vein authentication device according to claim 3, wherein the near-infrared light irradiation source includes a light source for acquiring an image picking up a portion of the fingerprints and a light source for acquiring an image picking up a portion of the venation, and the imaging control part controls irradiation of the near-infrared light by switching the light source used for irradiation.

6. The vein authentication device according to claim 1, wherein the authentication part performs, in addition to authentication processing based on the vein pattern, authentication processing based on the image of the fingerprints synthesized by the image synthesis part.

7. A vein authentication method of performing authentication based on a vein pattern of venation positioned inside a finger by irradiating a finger surface with near-infrared light, comprising the steps of:

imaging a portion of the finger surface continuously by an imaging part including a lens array having a plurality of light receiving lenses disposed like an array and is divided into an area to receive the reflected light and an area to receive transmitted light after passing through the venation, a near-infrared light irradiation source provided at an edge on a side of the area to receive the reflected light of the lens array to irradiate the finger surface with near-infrared light, and an imaging device for generating an image picking up a portion of the fingerprints based on the reflected light and generating an image picking up a portion of the venation based on the transmitted light, wherein a focus position of the light receiving lens positioned in an area where the reflected light is received is set at a position of the finger surface;

detecting a motion vector of the fingerprints based on a plurality of images picking up a portion of the fingerprints;

synthesizing images picking up a portion of the fingerprints based on the motion vector of the fingerprints to generate an image of the fingerprints and synthesizing images picking up a portion of the venation based on the motion vector of the fingerprints to generate an image of the venation;

extracting a vein pattern from the image of the venation; and performing authentication processing based on the extracted vein pattern.

\* \* \* \* \*